US006666857B2

(12) United States Patent
Smith

(10) Patent No.: US 6,666,857 B2
(45) Date of Patent: Dec. 23, 2003

(54) INTEGRATED WAVEFRONT-DIRECTED TOPOGRAPHY-CONTROLLED PHOTOABLATION

(76) Inventor: Robert F. Smith, 3714 Henley Dr., Pittsburgh, PA (US) 15235

( * ) Notice: Subject to any disclaimer, the term of this patent is extended or adjusted under 35 U.S.C. 154(b) by 0 days.

(21) Appl. No.: 10/057,880

(22) Filed: Jan. 29, 2002

(65) Prior Publication Data

US 2003/0144650 A1 Jul. 31, 2003

(51) Int. Cl.[7] ............................................. A61B 18/20
(52) U.S. Cl. ............................... 606/12; 606/5; 606/11
(58) Field of Search ............................. 606/4–5, 10–12

(56) References Cited

U.S. PATENT DOCUMENTS

| | | | | |
|---|---|---|---|---|
| 5,624,437 A | * | 4/1997 | Freeman et al. | 606/5 |
| 6,199,986 B1 | * | 3/2001 | Williams et al. | 351/221 |
| 6,271,915 B1 | * | 8/2001 | Frey et al. | 356/124 |
| 6,394,999 B1 | * | 5/2002 | Williams et al. | 606/5 |
| 6,500,171 B1 | * | 12/2002 | Williams et al. | 606/5 |
| 6,508,812 B1 | * | 1/2003 | Williams et al. | 606/5 |
| 2002/0007176 A1 | * | 1/2002 | Campin et al. | 606/5 |
| 2002/0082590 A1 | * | 6/2002 | Potgieter | 606/4 |

* cited by examiner

Primary Examiner—Michael Peffley
Assistant Examiner—Henry M. Johnson

(57) ABSTRACT

A system and method combining wavefront analysis with narrow-beam scanning photoablation where optimal corneal topography is first calculated then followed by real-time topographic feedback controlled photoablation. Eye movement and beam position sensing to within a tolerance of 5 μm are provided by high speed digital computation in conjunction with specialized charge coupled devices. Lasers of three different wavelengths—one low-powered pulsed ultraviolet, a second continuous visible band type, and a pulsed infrared type are combined together into narrow beams whereupon a scanning mechanism generates coaxial collimated beams for the functions of ablation, beam position sensing, and fundus spot imaging. Transepithelial ablation is performed utilizing the same CCD used for wavefront analysis by switching between two dichroic mirrors. The light source for the raster videokeratography topography means is the UV laser used for ablation.

20 Claims, 7 Drawing Sheets

INTEGRATED WAVEFRONT-DIRECTED TOPOGRAPHY-CONTROLLED PHOTOABLATION

BACKGROUND OF THE INVENTION

A review of the prior art reveals several US patents that define the status of scanning spot laser ablation and or eye-tracking systems. Lin, in U.S. Pat. No. 5,520,679, describes a scanning laser system and method of beam placement to produce smooth ablated surfaces; no compensation for eye motion, saccadic or other, is disclosed nor is there any feedback mechanism for controlling the location of the beam. Frey et. al, in U.S. Pat. Nos. 5,632,742, 5,980,513 puts forth a LADAR based eye-tracking apparatus in conjunction with a scanning excimer beam ablation system. Knopp et. al, presents in U.S. Pat. No. 5,865,832 a 2-axis servo-controlled mirror for tracking eye movement. Hohla in U.S. Pat. No. 5,645,550 uses a semi-rigid marking structure placed on the periphery of the eye.

These referenced patents are all implemented in analog form. The Frey and Knopp patents utilize contrast differences of eye tissue alone without the use of any external marking means; Frey selects the iris and pupil boundary while Knopp uses the iris and sclera boundary as the reference means for determining lateral (transverse or radial) eye position variations. In Frey's approach, the pupil must be maintained in the dilated state. Knopp, in utilizing PSD's (position sensing devices), averages the contrast of several portions of the iris/sclera boundary. While both systems under ideal conditions are capable of high eye tracking accuracy, the ablation procedure can produce changes in contrast across the stromal surface and thereby degrade the tracking precision. The Hohla patent presents an externally applied aiming assistance means for reducing such contrast variations, but does not specifically disclose means for achieving adequate speed in the tracking of saccadic eye motions.

Recent work in the field of evaluating overall optical performance of the eye using wavefront techniques (for example Williams et. al. U.S. Pat. No. 6,199,986) have presented means for determining the distortions of corneal surface and the other optical elements of the eye in terms of mathematical functions know as Zernike polynomials. PRK has been performed using the topography information provided by such wavefront techniques with considerable success in patients having slight to moderate myopia. A high degree of precision is required in locating the laser beam on the cornea and in determining the duration of ablation to produce the desired customized corneal surface. Real time topography measurement would greatly facilitate such customized ablations by insuring that the desired corneal topography is achieved.

A prospective system for performing PRK is one where the desired anterior corneal surface is sculpted with such a minimum of trauma that the surface topography immediately after ablation remains permanent thereafter, that postoperative discomfort is negligible and that after the regrowth of the epithelium, the wound healing response results in no corneal haze and the acuity of vision is retina and diffraction limited only. It is intuitive that for each laser-ablating pulse, minimizing the amount of energy delivered will also minimize the amount of phononic shock, heating and other traumatic effects on the cornea. The intensity of the pulse, i.e. the energy per unit area, must be above a threshold value, typically 50 $mJ/cm^2$ for 193 nm, in order to break the molecular bonds of the stromal cellular structure. At an intensity of about 150 to 200 $mJ/cm^2$, the per pulse ablation depth for stromal tissue averages 0.25 $\mu m$. In prior art, this relatively constant per-pulse ablation depth provides an a priori means for predicting the resultant ablation depth, such a procedure being necessary in the absence of a real time topographic measurement apparatus. Lower intensities that could minimize trauma would require a longer operation time and would result in a very uncertain prediction of tissue removal. Minimizing the cross-sectional area of the ablating laser beam also can result in reduced trauma and also reduce the cost of the laser because the per pulse energy can be lowered thereby requiring a smaller laser that may take the form of a solid state frequency-multiplied laser or a small excimer laser. The minimization of intensity/fluence and beam crosssectional area is limited by the need to perform the desired ablation quickly enough to avoid excessive stromal dehydration and patient stress. A solution to minimizing operating time would involve maximizing the laser pulse rate. Such an approach places an increasing demand on the bandwidth of the laser beam scanning system and the real time topography system.

In most existing PRK procedures, the corneal epithelium is removed by mechanical and/or chemical means in order to expose the stroma for laser ablation. Swelling of the cornea has been observed using such techniques. In Hohla (U.S. Pat. No. 6,090,100), a method for removal of the corneal epithelium via excimer laser is presented wherein a dye, which is absorbed by the epithelium and not by the stroma, fluoresces in the presence of excimer radiation to guide selective epithelium removal. However, the use of a broad laser beam subjects the overall cornea to the same shock trauma encountered in general broad beam PRK. A narrow scanning laser beam is desirable to minimize such trauma along with removing the need for the fluorescent dye for the procedure of epithelial ablation.

The present invention addresses the foregoing items and proposes to meet the goals outlined within the state of the art of existing technology.

SUMMARY OF THE INVENTION

The system and method of the present invention generally comprise:

A pulsed laser operating at a high pulse rate producing a narrow beam of ablating radiation having a wavelength in the region of 193 nm; this pulsed beam combined collinearly with a similarly narrow continuous laser beam, the combined beam then directed to a two-axis electromechanically-controlled tiltable mirror whereupon it is reflected to a parabolic mirror (paraboloid) which collects the combined beam paths reflected from the tiltable mirror and collimates them after which they are separated by a wavelength selective means—the pulsed laser radiation scanning beam being directed normally to the surface of the ablatable object (anterior cornea of the eye) and the continuous laser beam directed to a two-dimensional photodetection device which generates feedback voltage signals to control the tiltable mirror, an annular scleral mask with inscribed reference markings which is fitted over the eye, the mask leaving the cornea exposed to the collimated rays of pulsed radiation, the reference markings imaged by an objective lens onto a photodetector array of linear pixel elements, the photodetection signals used to control the tiltable mirror to compensate for translational and rotation eye movement; the mask being attached prior at the outset so that a wavefront means can be used to measure the optical distortions of the eye whereupon a corneal surface is calculated to correct the distortions;

a raster videokeratography topography system utilizing a portion of the excimer/ablating laser radiation to project a raster pattern on the semi-diffuse surface of the cornea undergoing photoablation, the diffusely reflected pattern then optically imaged onto a two dimensional photodetector whereupon it is digitized and the surface topography calculated;

the wavefront means utilizing the same components of the beam scanning system to produce the requisite collimated rays for retinal image mapping and optical analysis;

a control system performing the following functions: Sensing tiltable mirror position and through an analog high frequency loop and a digital mid/low-frequency loop, positioning the mirror to achieve beam positioning precision exceeding that of prior art; sensing the position of the cornea and adjusting the beam position to the desired precision within 0.0005 second; monitoring the topography a minimum of 5 maps per second to provide feedback control of the ablating beam;

the control system incorporating digital algorithms to perform the functions of: Computing the areas of the cornea to be ablated in a manner to optimize speed while minimizing trauma; interpreting a photoelectronically imaged raster to produce real time topography measurements; interpreting the eye motion sensor data to measure corneal radial translational deviations and corneal radial rotational deviations.

The present invention is principally distinguished from prior art in that it combines into a single stand-alone system the functions of wavefront analysis and small-spot scanning laser photoablation controlled by real-time topographic measurement. The wavefront analysis means produces an ideal target corneal topography which is used as a template to direct the ablation process, feedback controlled by real-time topographic measurement means, until the error between the template and ablated cornea is negligible.

Also distinguishing the present invention is the ability to employ a low-cost ablating laser, where the cost of the laser is lower not only because of the narrow beam—hence requiring lower pulse energy—but because there is no necessity for high beam-intensity uniformity or high pulse-to-pulse energy constancy. The ability to be able to monitor almost continuously the corneal topography changes during ablation and also direct the beam with great accuracy to a moving cornea thereby enabling immediate correction, allows for considerable tolerance in such laser properties.

The present invention relates to and expands upon two prior patents issued to myself. In U.S. Pat. No. 5,350,374 a broad excimer laser beam is segmented by a two-dimensional excimer light modulator means into a multiplicity of collimated narrow sub-beams each being directed to a corresponding sub-area of the cornea and coinciding with a grid point projected from a videokeratography system. The depth computed from the imaged position of each raster point then serves as a real-time feedback signal to control the associated ablating sub-beam on a pulse-by-pulse basis. A disadvantage in this prior art is the difficulty in fabricating the modulator means to be able to withstand the intensity of the broad laser beam—a problem further aggravated by the need of a very high pulse rate to avoid using more than one sub-beam per pulse—which would negate the sought-after advantages of the narrow beam scanning concept. The present invention attempts to obviate this limitation while retaining the real time topographic control concept embodied in the prior patent. In U.S. Pat. No. 6,024,449, a real-time videokeratography system is disclosed which utilizes a laser raster projector technique that minimizes topographic errors due to variations in the axial position of the corneal surface. The present invention's preferred embodiment uses one of the alternate embodiments of the prior patent; specifically, a portion of the output of the pulsed excimer laser used for photoablation becomes the source for the projected raster pattern on the semi-diffuse surface of the ablatable object. Because the laser pulse duration is in the nanosecond range, each raster pattern projected on the object (corneal) surface and then imaged on the two-dimensional CCD, results in a topography measurement unaffected by saccadic eye movement; further, the short wavelength improves the resolution of the raster pattern relative to visible light and the relatively low spatial coherence of the excimer reduces the adverse effects of speckle.

In attempting to further minimize the trauma accompanying PRK, photoablative removal of the epithelium (transepithelial PRK) using the narrow-beam scanning technique is incorporated into the overall PRK procedure of the present invention. An inherent fluorescent spectral component that characterizes epithelial photoablation is filtered and imaged on a CCD. When this spectral component essentially vanishes over the area of the cornea, removal of the epithelium has been accomplished whereupon real-time topography controlled ablation of the stroma can proceed.

A preferred embodiment of the invention incorporates the following:

1. A low per pulse energy (5 to 10 milli-Joules) excimer or solid state laser capable of operating up to approximately 1000 pulses/sec at a wavelength and pulse duration optimizing corneal photoablation.
2. A 2-axis servo-controlled flat mirror kinematically designed such that a coaxial/collinear beam, comprised of continuous wave laser radiation in the visible band and the pulsed laser radiation in the ultraviolet, impinges at the pivot point of the mirror such that the mirror position directly above the pivot point is invariant as the mirror is tilted along either or both axes. The beam is then reflected to a parabolic mirror whose focal point is at the pivot point of the mirror. Then the paths of the beam reflected from the parabolic mirror will all be collimated—parallel to one another—and deflected to a broadband polarizing beam splitter (BPBS) which transmits the pulsed 193 nm radiation component to the ablation target (anterior of cornea) while reflecting the continuous wave radiation to a 2-dimensional photodetecter, the latter taking the form of a specialized charge coupled device (CCD) called a charge injection device (CID). Because there is a one-to-one correspondence between the continuous wave laser beam position on the CID and the excimer laser beam on the radial/transverse direction of the ablation target, a means is obtained for determining, and thereby controlling, the position of the excimer laser beam on the cornea to within 5 $\mu$m—although a small number, is readily obtainable using a 10 mm diameter uniformly-distributed array of some 500,000 pixels and applying simple pixel interpolation. The CID is essentially a CCD that reads out only selected pixels so that by using the voltages from the mirror position detectors (electret sensors) to select a small area of pixels (perhaps 5 by 5), the intensities of those pixels can be two-dimensionally interpolated to locate the beam with the desired accuracy. A programmable logic device (PLD) digitally computes the coordinates of the beam position within about 40 μsec. whereupon the coordinates are converted into analog form and compensated by analog circuitry before being fed into the each of the mirror-actuating amplifiers for orthogonal negative feedback control of the tiltable mirror. Presently available PLDs can perform some 500 million floating point instructions per second, and it is this capability that, in conjunction with high speed CCD readout and analog to digital and digital to analog conversions that enable their incorporation to meet the real time control demands of the present invention.

3. An all-analog damping feedback loop using the electret sensors detecting tilt in each axis of the 2-axis mirror; these sensors' output being amplified using low noise wide bandwidth operational amplifiers. A large value of negative derivative feedback critically damps out the resonances of the mechanical portion of the system, increases the bandwidth an order of magnitude above the dominant resonant frequency of the mechanical system, reduces non-linearities of the electromechanical system, and reduces the effects of external vibrational forces.

4. A high speed videokeratography system for measuring corneal topography utilizing the excimer laser as the light source for the raster pattern projection. Then by focussing this 193 nm wavelength diffuse light pattern on the cornea onto a back-illuminated charge coupled device (BCCD) sensitive to the 193 nm radiation, a topographic resolution of nearly a micron can be achieved. A digital algorithm generates instantaneous topography measurements over a grid of nearly two thousands points on a cornea undergoing ablation, enabling full topography surface measurements of at least 5 times a second over the course of the ablation procedure. Rapidity of measurement enables the use of averaging and regression techniques to maximize accuracy. This high speed also facilitates integrating the topography system into real-time feedback control of the ablation system.

5. A digital-analog (hybrid) eye tracking system enabling precise ablative beam positioning on the cornea regardless of positional variations such as characterized by the saccades of the in-vivo eye. The same lens used to image the raster pattern on the BCCD is also used to focus the corneal mask reference markings onto a photodetector constructed by a series of linear charge coupled devices to form what is herein referred to as a segmented charge coupled device (SCCD). Analog voltages corresponding to pixel intensities of the markings are converted to digital form, and by means of a digital algorithm, the instantaneous position (in x-y coordinates) in digital form is converted into two analog voltages—orthogonally controlling the tiltable mirror, and after being phase compensated, each voltage is summed into the actuating amplifier controlling the tiltable mirror thereby insuring that the ablating beam is always directed to the desired position on the cornea of the eye.

6. Digital algorithms, written to minimize execution times of the a) beam detection/positioning algorithms, b) topography calculation algorithms.

7. A wavefront analysis means integrated within the apparatus of the invention whereby the continuous beam laser is used to direct the same collimated beams (absent the pulsed laser component) to the pre-operative eye, with the resulting retinal spot images being imaged on the same CCD used for epithelial ablation. Because the eye-tracking means of the invention is activated, the absolute spot positions the retina can be very accurately located. Then in combination with corneal topography (using the existing system in conjunction with a fluorescent dye on the pre-operative eye) whereby the pre-operative localized corneal curvature at the point of corneal entry for each beam is calculated, the desired post-operative corneal curvature is determined—i.e., the corneal topography required for perfect (diffraction limited) focus of the collimated rays on the retina.

DETAILED DESCRIPTION OF THE INVENTION

Figure 1:
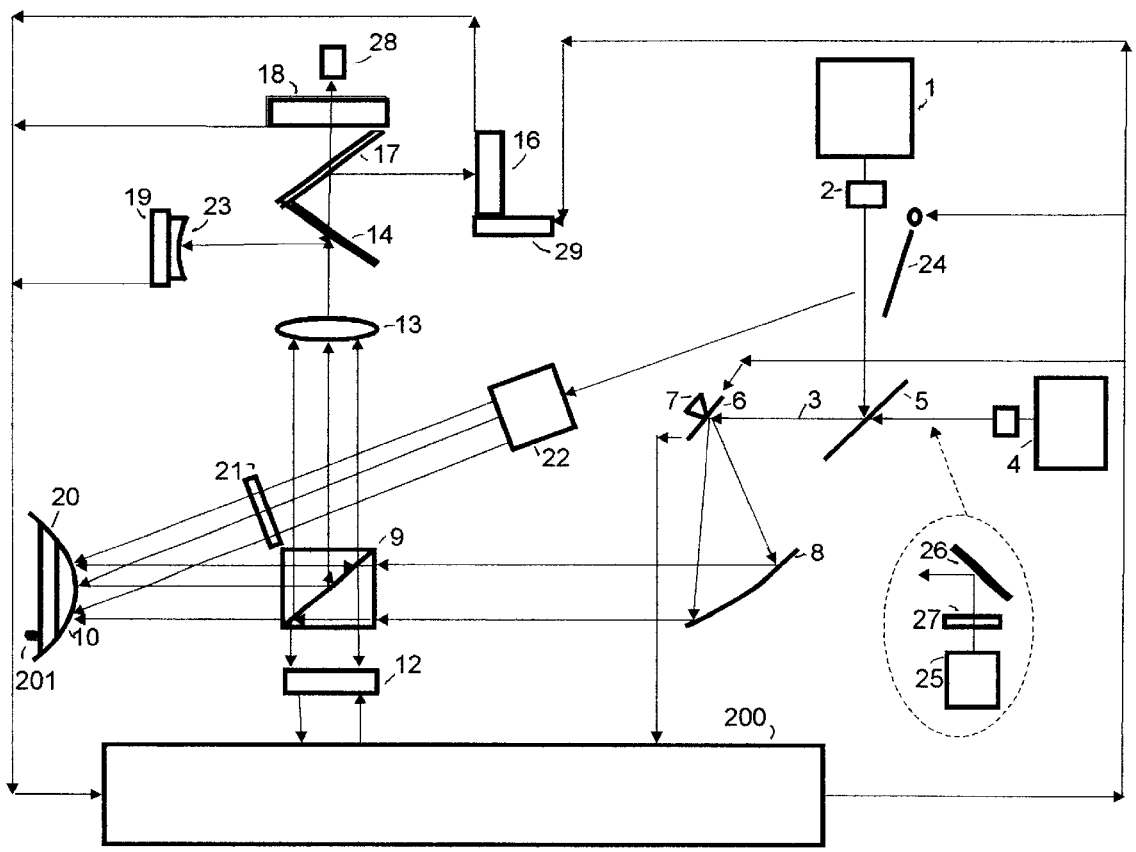
FIG. 1 shows in functional form the basic constituents of the preferred embodiment of the invention.

The preferred embodiment of the invention shown in FIG. 1 is detailed as follows: The ablating beam emanating from a high pulse rate 193 um excimer laser 1 having a per-pulse energy of 5 to 10 mJ is directed to a recollimating/beam-shaping device 2 which in addition also functions as a controllable attenuater. The emerging circular cross-section beam is then directed to a planar dielectric mirror 5, which is essentially totally reflective to the excimer radiation but mostly transparent to visible and/or infra-red light. A continuous wave 532 nm laser 4 classified as a diode pumped solid state type operating at about 5 mW, having a beam of about the same circular cross-sectional area as the pulsed laser beam (i.e. a diameter of about 0.5 mm), is directed through mirror 5 and collinearly combined with the pulsed excimer laser beam. The combined beam 3 is then directed to a 2 axis servo-controlled tiltable mirror 6 which equally reflects both components of beam 3. By directing beam 3 at the pivot point 7 of mirror 6, the reflected beam will appear to emerge as a cone of rays emanating from a fixed focal point for a multiplicity of tilt mirror positions. Using the principle of parabolic mirror reflection, a means is obtained for directing the excimer laser beam to any part of the cornea along paths parallel to the optical axis of the eye. Accordingly, mirror 8 is an off-axis paraboloid that reflects the cone of rays emanating from tiltable mirror 6 to form a collimated cylinder of rays having a cross-sectional size necessary to cover the cornea. Beam paths comprising this cylinder are then reflected to the BPBS 9. Because both pulsed and continuous laser beams will be substantially plane-polarized, then by radially rotating the axes of the lasers 90° with respect to each other, the BPBS 9 will transmit the ablating beam directly to the cornea 10 with mimimum attenuation while mostly reflecting the continuous beam to charge injection device CID 12 which facilitates very rapid and precise tracking of the continuous laser beam and, concomitantly, the pulsed laser component of the beam. It is to be noted that under the constraint of existing art, BPBS 9 will be optimized for maximum transmission of the 193 nm component but permitting a finite (but small) portion of the continuous laser component to reach the cornea.

Real time topography is integrated into the system of the present invention by means of a hinged mirror 24 which diverts a selected excimer laser beam pulse to a beam expander 22 whose function is to expand and diverge the beam to a crossectional area slightly larger than the cornea 10 of the eye (in accord with U.S. Pat. No. 6,024,449.) The resulting beam is then passed through a raster projecting grating (Ronchi grating) 21, and then onto the cornea 10. The separation between the Ronchi grating and the cornea is maintained as closely as possible without occluding the ablating laser beam in order to minimize Fresnel diffraction effects. When undergoing photoablation, cornea 10 reflects both a diffuse and a specular raster image to BPBS 9. By rotationally orienting the raster projection beam so that the specular reflection component is transmitted through BPBS 9, then the diffuse image, which is unpolarized, will be polarized and directed to focussing lens 13. The converging rays of lens 13 are reflected by a dielectric mirror 14 onto CCD 19 which is sensitive to the wavelength of the pulsed excimer laser radiation. Hinged mirror 24 is activated electromagnetically or electrostatically at a speed sufficient to capture a single laser pulse; when unactivated, mirror 24 rests in a position that does not interfere with the normal path of the pulsed laser beam used for ablation.

Lens 13 is multipurpose in that it images the diffusely reflected raster pattern of the topography system, the reference markings of mask 20, the 460 nm radiation occurring during epithelial ablation and the spot images on the fundus during wavefront analysis. It is biconvex with a hyperboloidal front surface and is transparent for wavelengths from 193 nm to about 1000 nm. Because of the curvature of the cornea, focussing of the raster image on CCD is improved using a field flattening lens 23, which is aspheric concave-planar. The design of both lenses 13 and 23 follow from the objectives put forth in U.S. Pat. No. 6,024,449.

The components of the eye tracking system primarily comprise: Annular mask 20 which is attached to the sclera of the eye by means of small projections 201 into the epithelial layer to ensure negligible movement between the eye and mask; monochromatic reference markings (using for example cadmium sulfide) on mask 20 that produce a bright yellow emission (570 nm); BPBS 9 which is sufficiently reflective of the emission from the reference marks on mask 20 that they can be imaged by lens 13 on SCCD 18; dielectric mirror 14 which is transparent to the emission of the reference markings; dichroic mirror 17 which also transmits the 570 nm reference marking images.

Transepithelial ablation is performed by the means consisting of dichroic mirror 17 and CCD 16. Dichroic mirror 17 reflects only the emissions in the region of 460 nm thereby enabling the monitoring of the presence of epithelial tissue so that the ablating beam will continue to erode only those areas where epithelial tissue is present. Coordination between the beam position sensing (CID 12) and eye position sensing (SCCD 18) permits the accurate removal of epithelial tissue.

In order to integrate a wavefront analysis means within the apparatus of the preferred embodiment, several special factors must be taken into account. First, it is noted that the more common application of the of wavefront analysis (i.e. the Shack-Hartmann technique) is to project simultaneously a pattern of narrow collimated beams through the eye onto the retina/fundus whereas in the present invention, only one collimated beam at a time is projected. Therefore, the exact corneal coordinates at the instant of capturing each fundus spot image must be determined thereby mandating that the eye tracking system be maintained at a high level of precision. Secondly, because it is difficult to differentiate between pure radial/translational eye movement and rotational movement (i.e. the eye in the socket rotating about vertical/horizontal axes versus movement in the plane normal to the optical axis of the eye), each spot measurement must be made when the eye is in the same position. Thirdly, because the beam spots on the fundus are viewed as diffusely reflected images, the use of a high spatial coherence laser can cause image deteriorating speckle, so it is necessary to employ a low spatial coherence beam source of the type discussed in U.S. Pat. No. 6,199,986 wherein a super luminous diode (SLD) having a wavelength of 780 nm is selected. In view of the foregoing constraints, wavefront analysis is implemented as follows: In the dashed oval of FIG. 1 is shown the SLD 25 which includes a beam collimator, a mirror 26 which is either partially reflecting or dichroic that combines the beam from the continuous laser 4 with the SLD beam. A shutter 27 (electro-optical or mechanical) is triggered from the control system 200 when the eye position is sensed to be within the prescribed tolerance. Because the light output from the SLD is continuous, the shorter the duration the shutter is opened, the lower the intensity of infrared light spot images on the retina/fundus. Therefore, a compromise must be made between imaged spot intensity and shutter speed. Fortunately, the speed of the eye-tracking enables shutter 27 to be open for a longer duration because some 30,000 eye position measurements can be made per second so that, as long as the eye position is within the allowable band, the spot image light continues to be collected (integrated) by the sensor device which for this embodiment, is CCD 16. As soon as the band is exceeded, the light integration period on CCD 16 is terminated and, if the integration period is long enough (e.g. 2 milliseconds), the spot image on CCD 16 is recorded. It is pointed out that for the 780 nm SLD light to reach CCD 16 relatively unattenuated, dichroic mirror 17, used for epithelial ablation detection, must be switched to a dichroic which transmits 570 nm and reflects 780 nm. Although the resolution requirements when used for controlling transepithelial ablation are relatively moderate (20 $\mu$m or so), wavefront measurement accuracy must be within 5 $\mu$m on both the fundus measurement (CCD 16) and the eye-movement measurement (CCD 18).

A complete wavefront measurement involves the capturing of some 200 fundus spot images. Within the present embodiment of the invention, this measurement could be completed in less than a second. However, under conditions of considerable eye movement, a much longer time may be required. To minimize this measurement time, it is desirable to provide a comfortable fixation target for the patient so as to increase the probability that the eye will be in the desired position. Because there are no sensor elements in the center of SCCD 18, a central hole located here enables viewing a fixation target means 28 consisting of a light source, transparent (bulls-eye) target, and lens. Before initiating the wavefront analysis, the lens in 28 is adjusted for the sharpest patient-perceived target image.

Rays of light re-emerging from the fundus spot images are somewhat collimated by the optics of the eye, so that after being reflected by BPBS 9 to lens 13 and passing through dielectric mirror 14, subsequent reflection from mirror 17 results in their being focussed much closer to lens 13 than is the case for imaging diffuse reflections from the cornea during the course of epithelial ablation. Therefore, CCD 16 is mounted so that it may be mechanically translated by a servomotor translation device 29 until the blur size of the fundus spot images focussed on CCD 16 is minimized. It is then a simple matter to correlate the axial position of CCD 16 with a diopter change that would be required to be made to the corneal curvature to yield best achievable focussing. Then from the global corneal curvature obtained by the pre-operative topography measurement, the best global corneal curvature can be calculated. If the other optical elements of the eye (i.e. posterior of cornea and the lens of the eye) were perfect, this best global corneal curvature would provide the desired best vision. However, because irregularities can occur in the aforementioned elements, the blur image will not be optimally minimized regardless of the perfection of the anterior cornea, and it is by means of the wavefront measurement technique that the anterior corneal surface may need to be modified to achieve the sought-after best vision. If irregularities in the anterior cornea are excessive, an accurate calculation of desired topography is not feasible—in which case, corneal ablation would first be performed to achieve the global curvature determined for best possible focus and, some days after re-epitheliazation of the cornea, the wavefront measurement would be repeated after which it would be expected that spot fundus positions could be reliably correlated to local corneal curvatures to enable determination of the final desired corneal topography. As an alternate in cases of large anterior cornea irregularities, a customized soft contact lens (after the teachings of U.S. Pat. No. 6,305,802) might be applied to enable successful wavefront analysis without the need for a pre-shaping corneal ablation prior to wavefront analysis.

Measurement of pre-operative corneal topography is a requirement for the wavefront method of this invention, so the real-time topography system, used during the ablation procedure, must be adapted as follows: Dielectric mirror 14, reflecting only the 193 nm wavelength, is switched to a 50—50 reflecting mirror so that the fluoresced yellow-green wavelength raster pattern resulting from a dye such as sodium fluoroscein, infused on the cornea and being irradiated by the 193 nm wavelength, can be imaged onto CCD 19 while the 570 nm radiance from the reference markings on scleral mask 20 are imaged onto SCCD 18. Although the wavelength range of the pre-operative topography and eye tracking overlap, interference does not occur because the areas of interest (i.e. scleral vs. corneal) do not overlap. It is not necessary that wavefront analysis and topography be conducted at the same time—a series of topographic measurements can be conducted (over several seconds) to define the apex of the cornea and from this reference point, the positional topography evaluated. However, to obtain highest accuracy the hinged mirror 24 should be activated for a topography shot only when the eye position is within the same allowable band specified for wavefront analysis.

Sensing signals from the four CCD devices and tiltable mirror in FIG. 1 are inputted into the overall control block 200 as indicated by the incoming arrows while output drive voltages are indicated by the outgoing arrows. Direction arrowed lines not connected to block 200 indicate only light paths. Block 200 performs the functions of analog-to-digital and digital-to-analog conversions, digital and analog control computations and control voltages for accomplishing the purposes of the invention.

Figure 2:
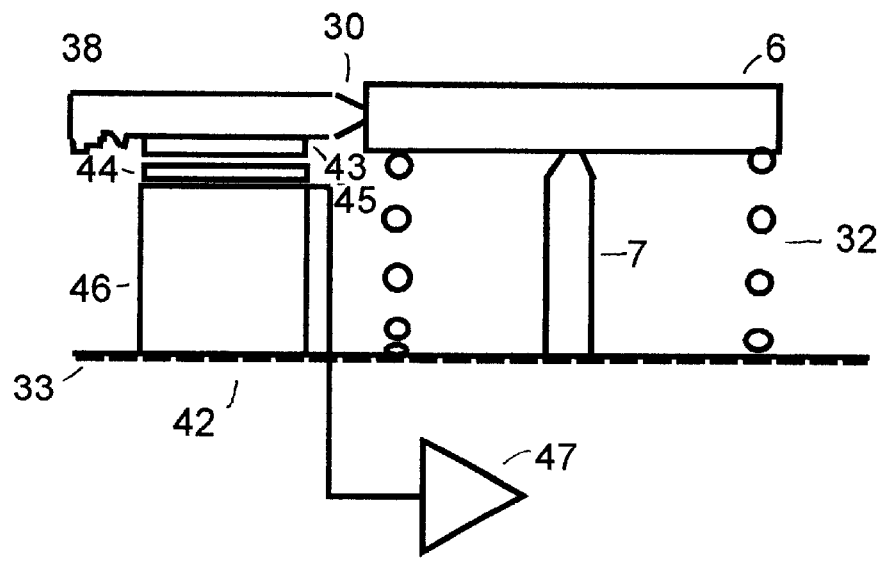
FIG. 2a is a side view of the tiltable mirror, its coil spring suspension, and central pivot post together with the orthogonal actuating pivots.
FIG. 2b is a top view of tiltable mirror showing the orthogonal actuating pivot locations.
FIG. 2c details the voice coil actuator assembly and the electret tiltable mirror position sensor.
Figure 2:
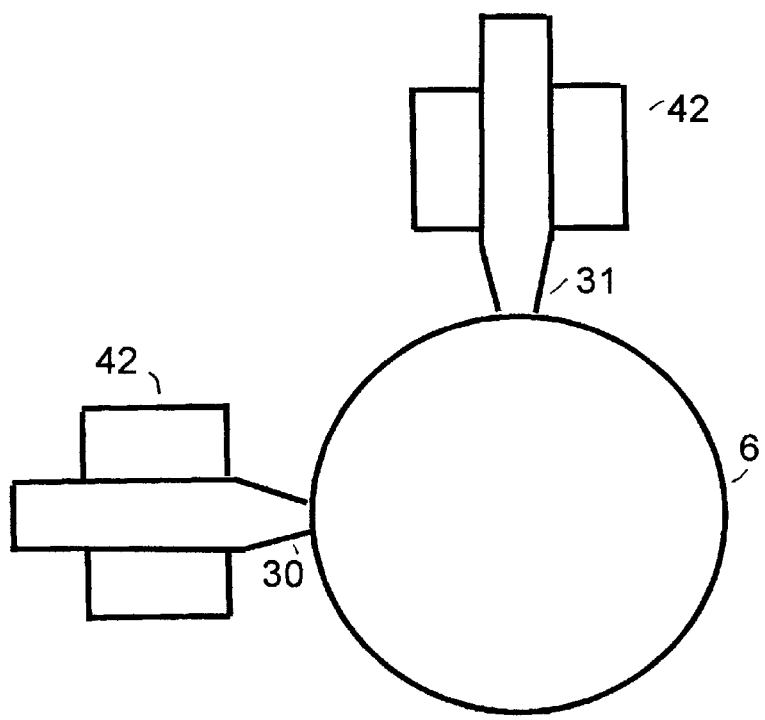

FIG. 2a shows a side view of the mechanical features of the circular servo-controlled tiltable mirror 6. A stiff pivot post 7 supports mirror 6 at its center and the location of the apex of the conical pivot hole is as close to the surface of the mirror as feasible while avoiding any distortion of the mirror surface. Two other conical holes are located on the rim of the mirror at points 90° apart with respect to the central pivot point. This kinematic design orthogonalizes motion of the mirror, in the plane of the mirror, resulting from movement of the actuating pivots 30 and 31. Thus, movement of pivot 30 produces deflection of the mirror only in the x-axis, while movement of pivot 31 produces deflection only in the y-axis. To insure the mirror 6 is maintained in firm contact with the pivot post 7, a coil spring 32 is firmly attached on one end around the rim of the mirror and the other end firmly attached to the foundation frame of reference 33. Spring 32 is maintained in tension and has a high enough spring constant to prevent any chatter between pivot post 7 and mirror 6, but low enough to minimize forces on pivots 30 and 31 over the range of desired dynamic deflection of mirror 6.

Figure 2C:
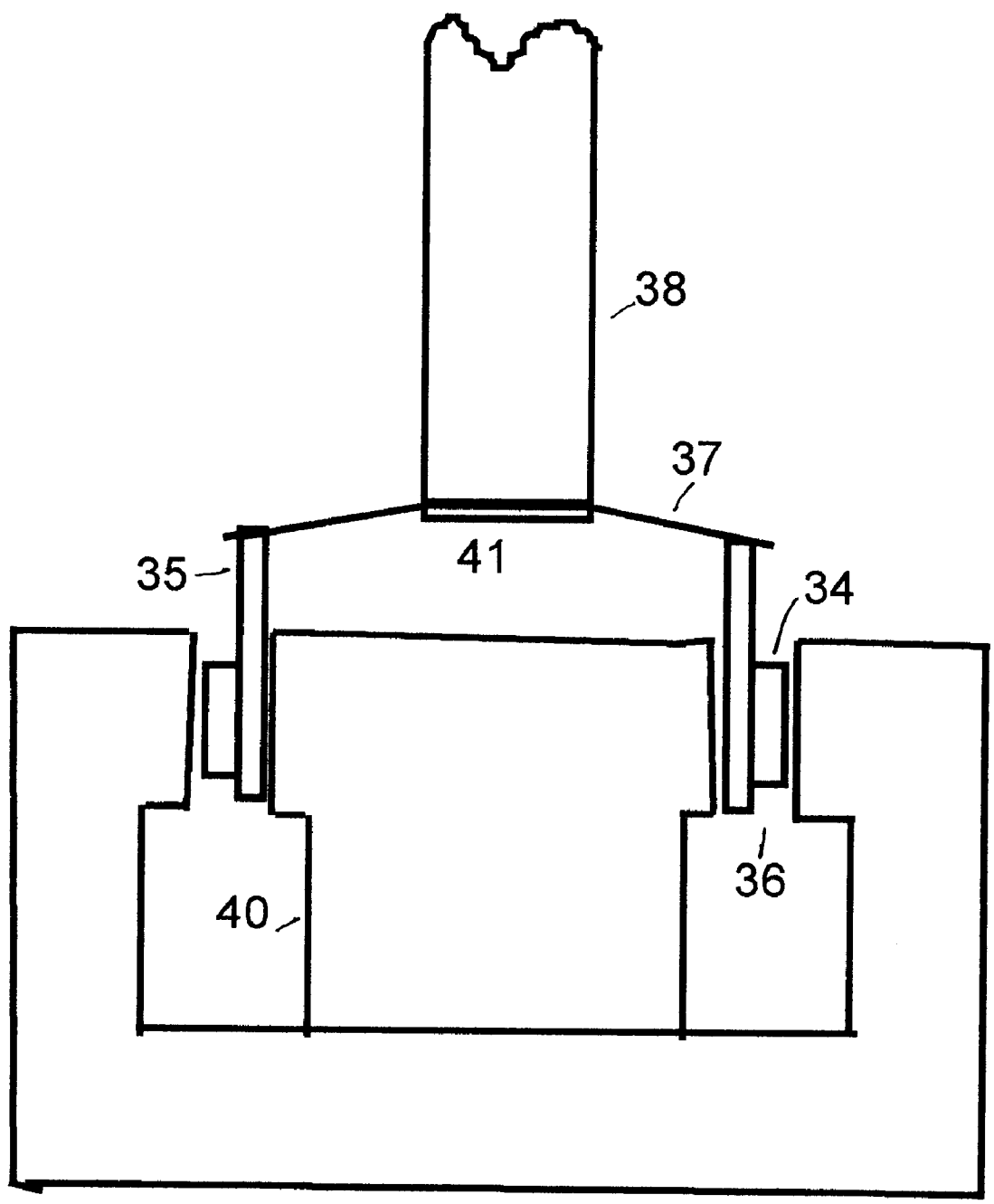

Features of the tiltable mirror actuating assemblage are shown in FIG. 2c. Similar to a permanent magnet loudspeaker, a coil 34 (equivalent to a voice coil) consisting of 120 turns of #38 copper wire is wound around an 8 mm diameter former 35 and then aligned and constrained radially within the airgap 36 by a compliant structure (spider) 37. Attached to the former 35 is a rigid L shaped arm 38 attached to an arm pedestal 41 at its one end, and at the other end the actuating pivot 39. It is desired to minimize the radial distance between the center of the coil 34 and the pivot post 7 so that the mass of all the moving elements is minimized (total mass of these translational elements is less than a gram) while their stiffness is maximized. Tiltable mirror 6 is also designed to have minimum mass (3 mm dia., 1 mm thick, preferably of titanium to have maximum stiffness). The principal natural frequency of the voice coil/mirror mechanical system is about 500 Hz—a bandwidth lower than required for adequate eye tracking. Negative feedback control techniques can greatly increase the bandwidth provided the actuating system is sufficiently responsive. Towards this end, advanced permanent magnet material such as neodymium-iron-boron in used for the cylindrical magnet 40 to yield an airgap flux of near 1 Tesla resulting in a force of some 500 grams per voice-coil ampere of current. It can be seen that increasing the separation between parabolic mirror 8 and tiltable mirror 6 increases the sensitivity (or gain) of the control system. A high sensitivity is desirable in that the movement of the tiltable mirror for a given beam deflection thereby reducing the power requirements of the control system; high sensitivity is undesirable because it gives rise to increased noise and stability problems. A separation of about 8 inches yields a reasonable compromise in sensitivity while insuring that the laser beams avoid excessive spreading due to diffraction.

FIG. 2b also shows the location of an electret sensor 42 which transduces the axial position of arm 38 to a voltage signal. There are 3 components of the sensor: The first is radial portion of arm 38 which is in the form of a rectangle (when view axially) that forms the top conductor 43 of the sensor 42; the second is the layer of electret material 44 deposited on bottom conductor 45; the third is the insulating block 46. The electret layer forms a constant charge on the conductive sheet 45 so that by the relations $Q=CV$ and $C=K/d$ where Q is the effective charge of the electret, V is the voltage on the conductive sheet 45, C is the capacitance between the top conductor 43 and bottom conductor 45, K is a constant, d is the separation between conductors 43 and 45, and V is the voltage between the conductors 43 and 45. Therefore, there is a linear relation between the voltage induced on conductor 45 and the separation d (so-called edge effects detract from a linear relationship between spacing d and voltage V, but provided that variations in d are small in comparison with the nominal value of d, departures from linearity are negligible.) This inherent linearity property of the electret sensor is of no benefit if it is not preserved by subsequent amplification before completing the feedback loop. Therefore, a low noise low drift operational amplifier 47 amplifies the electret sensor voltage to a sufficient level and high enough signal-to-noise ratio to provide the necessary analog feedback to increase the electromechanical system bandwidth and damping; also by correlating the two orthogonal electret sensor signals with approximate beam position on CID 12, a small region of pixels on CID 12 can be searched to rapidly determine exact beam position.

Figure 3:
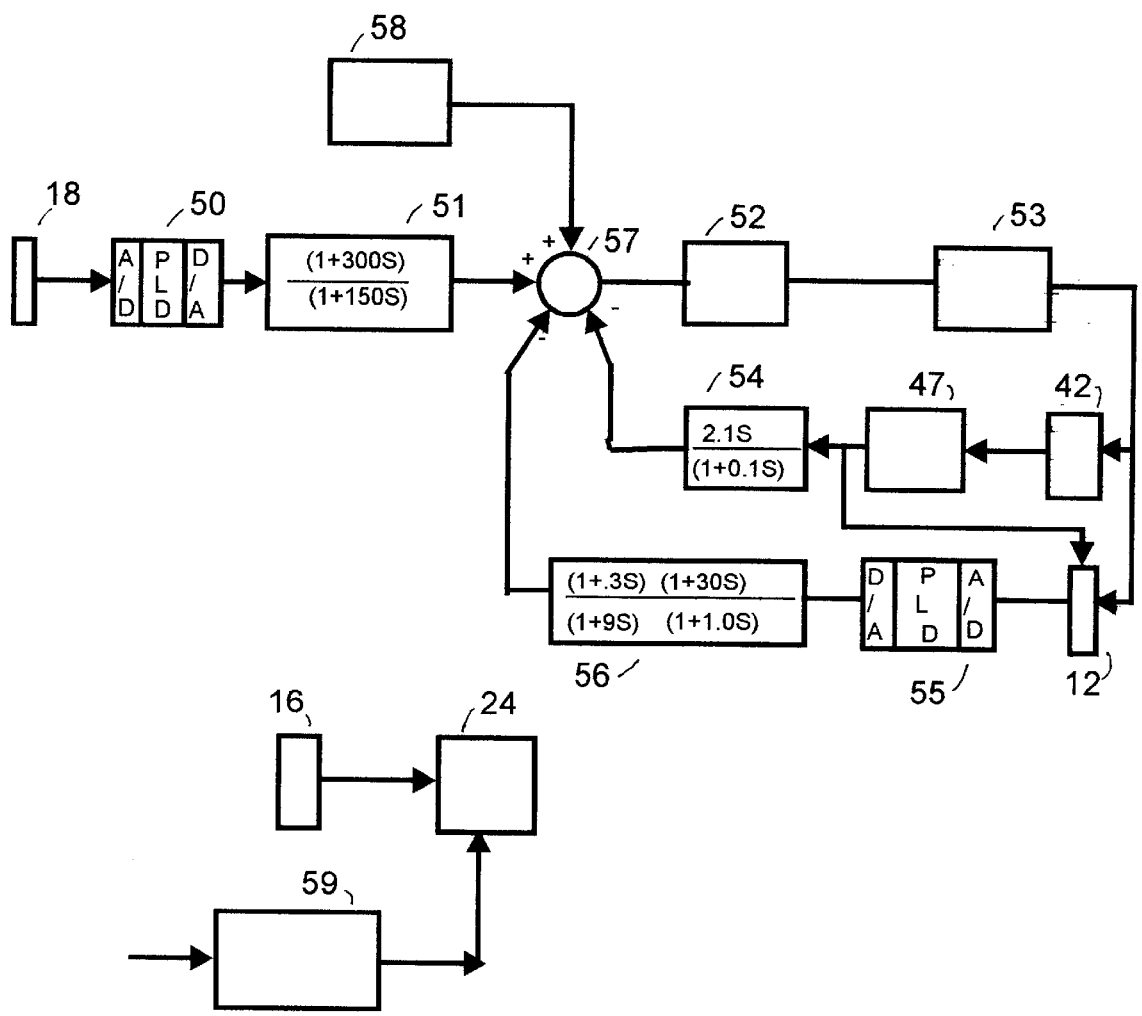
FIG. 3 is an operational block diagram giving the parameters of the transfer functions for one of the identical orthogonal axis controllers.

FIG. 3 is an operational block diagram detailing the analog and digital control components of the invention as denoted by block 200 in FIG. 1. It is noted that although there are two orthogonal drive units for the tiltable mirror 6, FIG. 3 shows only one because the other drive unit is identical. Starting with the analog voltage out of the eye tracking sensor SCCD 18, this voltage signal, representative of the intensities of the SCCD pixels for a single measurement frame, is inputted into block 50 where after conversion via an analog-to-digital converter (ADC 10 bit>100 mHz), it is operated on by a pre-programmed PLD that locates the intensity maximums corresponding to the locations of the reference marks on mask 20 and then solves these to yield the eye position along either the x or y axes; the digital positional value is converted via a DAC (12 bit, 200 mHz) and inputted into a lead/lag circuit—block 51—which functions as an anticipator of eye position to compensate for system time delays and is optimized by the values given in FIG. 3 where the delay between input and output of block 50 is about 30 $\mu$sec. This relatively small delay is achieved by use of the fact that from measurement to measurement, the distance between pixel intensity peaks is quite small, so the search for intensity peaks can be limited to few pixels of the linear CCDs comprising the SCCD. At summing block 57, the desired beam position outputted from block 58 is combined with the measured eye position signal out of block 51 and the derivative and positional feedback analog voltages and inputted into power amplifier 52. Because of the high efficiency of the voice-coil drives, the peak power requirement of amplifier 52 is low—about two watts, but the bandwidth must be high—around 1 mHz with a volts per volt gain of about 10. Such an amplifier is presently commercially available. The output of amplifier 52, and its associate, drive the voice coils contained within the electromechanical system, block 53, to provide orthogonal control of the tiltable mirror 6. The output of block 53 can be interpreted as both the x and y (orthogonal) components of tiltable mirror 6 position and also as the position of the collimated beam as it is projected onto the CID 12 sensor. In the former case, the electret sensor 42 voltage (and that of its orthogonal associate) is amplified and reduced in impedance by a low drift, very high input impedance operational amplifier 47 before being inputted to a passive derivative circuit—block 54 whose output provides the electromechanical system all-analog damping. This negative feedback damping loop contains no delay-introducing digital components. Amplifier 47 is also sent to CID 12 for the purpose of constraining the pixel readout to the area where the beam would be expected to fall. By so doing, locating the precise position on CID 12 can be very rapidly determined by interpolating localized pixels to find the point of maximum intensity. This process is performed by block 55 using a dedicated PLD for solving for the instantaneous beam position coordinates. These coordinates are then converted into analog form, compensated by passive lead/lag, lag/lead circuit 56 whose output is feedback into power amplifier 52, (the ADC and DAC are similar to those used for eye tracking). The high speed of the PLD and associated algorithm yields the analog output representative of beam position delayed by about 50 microseconds. Although small, this 50 $\mu$s delay is the main factor limiting the bandwidth of the control system; even so, using the input and feedback compensation time constants denoted in FIG. 3, the tracking error is confined to a few microns under conditions of maximum saccadic eye movement. All numerical values of the time constants in the transfer function blocks 51, 54, and 56 are given in microseconds: also the output of block 53 is in terms of radian tilt of mirror 6.

The overall control block 200 in FIG. 1 performs the following additional functions: To divert the excimer laser beam to the raster projection means, a trigger signal from the laser is detected indicating the time of the last pulse, then in preparation for the next pulse, a power source 59 is activated that drives mirror 24 to deflect a single excimer pulse from its normal path to beam expander 22 after which mirror 24 is returned to its normal position. Concurrently, CCD 19 is signaled to integrate the raster light-intensity pattern after which the analog signal of a frame of pixel intensities is returned to the control system. Also, for the wavefront measurement application, a fundus spot image, as captured by CCD 16 is minimized by driving the translation stage 29 to a position yielding the minimum pixel area.

Figure 4A:
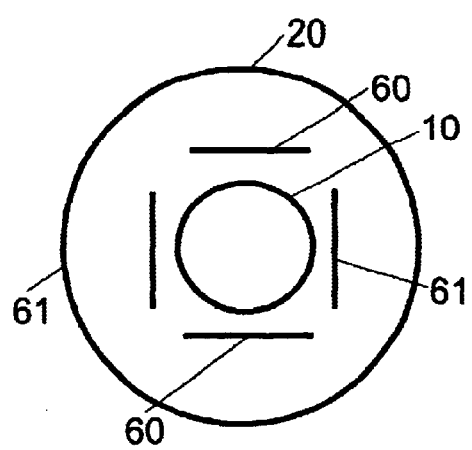
FIGS. 4a, b, c define the details of the scleral mask and SCCD for eye tracking.
Figure 4C:
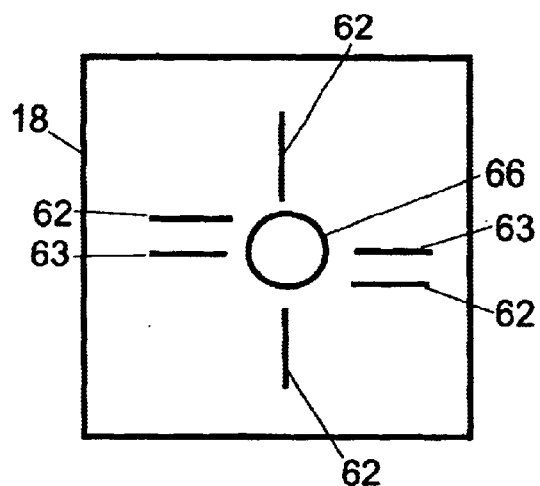
Figure 4B:
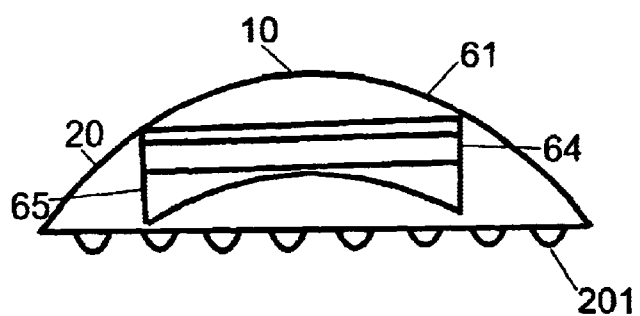

To further detail the elements related to eye tracking; a front view of scleral mask 20 is shown in FIG. 4a with one possible configuration of reference markings consisting of an open cross of fine line markings 60. These line markings are of a sufficient length to encompass maximum eye movements and as shown in the side view of FIG. 4b, the markings retain their dimensional stability by being applied to a rigid bar 64 (a titanium bar of about a 0.5 by 0.5 mm cross-section) which in turn is mounted on a semi flexible base 65 in the form of a wall about 0.5 mm thick curved along its base to conform with the eye-mounted scleral mask 20. Base 65 is flexible enough to conform to the sclera and by means of the projections 201, uniformly distributed throughout the underside of mask 20 and penetrating the epithelial layer, there is negligible movement between mask and eye is maintained. The eye tracking sensor element SCCD 18 in FIG. 4c is comprised of six linear charge coupled devices (LCCDs), each LCCD is about 1000 to 2000 pixels long—2 mm—and one pixel wide. SCCD 18 has a central hole 66 that permits the projection of a fixation target to the eye when wavefront analysis is being conducted. When the image of the reference marking is imaged by lens 13 onto the plane of the SCCD, the vertically oriented linear charge coupled devices—LCCDs 62—detect the position of the horizontally aligned markings 60 while the horizontal LCCDs 63 detect the position of the vertical markings 61. Rotation of the eye about its optical axis is detected by the remaining LCCDs 63 in the following manner: If the eye is unrotated from its nominal position, the location of maximum intensity along both LCCDs 62 and 63 will be the same regardless of the translational position of the eye. When rotation occurs, the angle of rotation is obtained by finding the distance between the intensity maxima of LCCDs 62 and 63, dividing by the normal distance between the two LCCDs and then taking the inverse tangent of this result. Then by applying the transformation of coordinates formula, the exact position of any point of the eye may be found. An eye position coordinate measurement rate of about 30,000 per second can be accomodated using this SCCD design. Such a rate is achieved by an interpolation algorithm that searches for intensity maxima among only a limited number of pixels in each of the LCCDs comprising the SCCD; this limited search allowed because the change in eye position in a 33 $\mu$sec time period is small even under conditions of the most severe saccadic eye movement.

The topography system in the present embodiment derives from an alternate embodiment disclosed in U.S. Pat. No. 6,022,249 wherein it was pointed out how diffraction effects cause a significant loss of resolution when projecting a pattern of collimated light upon a semi-diffuse object. The alternate solution to the problem proposed using a portion of the ablating excimer laser radiation as the light source of the projected raster pattern on the cornea. Because the wavelength of excimer radiation commonly used for corneal ablation is 193 nm, the resolution of the projected pattern is some three times higher compared to a visible light source.

The motive for using collimated light rather than employing an optical system to project the raster pattern on the cornea is two-fold: First, although a sharper raster pattern could be obtained with an optical projector, axial variations in eye position would result in transient blurring of the focussed raster pattern—the blurring due to diffraction using collimated light through a grating is relatively unaffected by eye position. Secondly, the requirement for a diverging beam—to nullify topographic measurement error due to axial eye movement—cannot be achieved with an image focussing means. An excimer laser source is further suited for performing videokeratography because the nano-second pulse duration obviates inaccuracies due to saccadic eye motion. Because of the deep-ultraviolet nature of the 193 nm radiation, the lens 13 must be fabricated from fluorite or equivalent glass and BCCD 19 must be fabricated as a back-illuminated type permitting detection of the 193 nm radiation. This raster pattern is imaged upon the cornea using a grating consisting of alternating vertical opaque and transparent bars (Ronchi grating). The grating selected for the preferred embodiment has 0.2 mm vertical bar spacings with 0.1 mm openings, for a total of about 50 bars. This ratio of transparent to opaque spacing (i.e. 1:1) eliminates even-order diffraction images. Placement of the grating 21 is at a distance of 22 mm from the apex of the cornea 10 and at an angle of 22° to the axis of the eye. This relatively close placement is a compromise between minimizing diffraction images while preventing any occlusion of the scanning ablating laser beam by the grating housing. It is noted that this Ronchi grating is actually a diffraction grating—however, in the present case, the grating spacing is some thousand times the wavelength of the excimer laser radiation, so rather than the first order diffraction images being displaced at a large angle (20° to 50° with respect to the axis of collimated light as is the case of normal diffraction gratings), the displacement is very small so that the first order image is nearly superimposed on the desired zeroth resulting in blurring and spurious distortions in the raster pattern. Fortunately, the first order images are only some 10% of the intensity of the zeroth order image resulting in intensity variations that are sufficiently uniform to permit the necessary measurement accuracy.

BCCD 19, in addition to being a back-illuminated type, is further distinguished from the typical two-dimensional CCD in that, rather than being composed of uniformly spaced sensor cells (pixels) across its detection area, this area comprises some 50 linear CCDs. Such a design is impelled by the following considerations: In order to achieve the desired goal of ± one $\mu$m topography measurement accuracy, a relatively close pixel spacing—about 500 pixels per mm of distance on the ablating surface is needed. For a circular measurement area of some 10 mm diameter, the number of pixels in the CCD would be approximately 20 million. Such a high pixel density would present a problem both in the fabrication of the CCD and in the readout and computational processing speed required. However, owing to the invariance of vertical raster points and axial position independence concepts developed in U.S. Pat. No. 6,022,249, only some 50 rows of 3600 pixels per row are needed to determine the surface topography over a 10 mm diameter circular area—i.e. some 2000 raster points, which excluded to a circular cross section, means processing only some 150000 pixels per full corneal frame resulting in a raster measurement precision of about 0.5 $\mu$m when pixel intensity interpolation is applied. Because present technology enables a pixel readout rate of at least $50 \times 10^6$ pixels per second, the analog voltage signal containing all of the pixel intensities is produced at the rate around 100 frames per second. The subsequent analog-to-digital conversion and digital processing using the PLD can produce some 10 full corneal surface topography measurements in one second.

Figure 5:
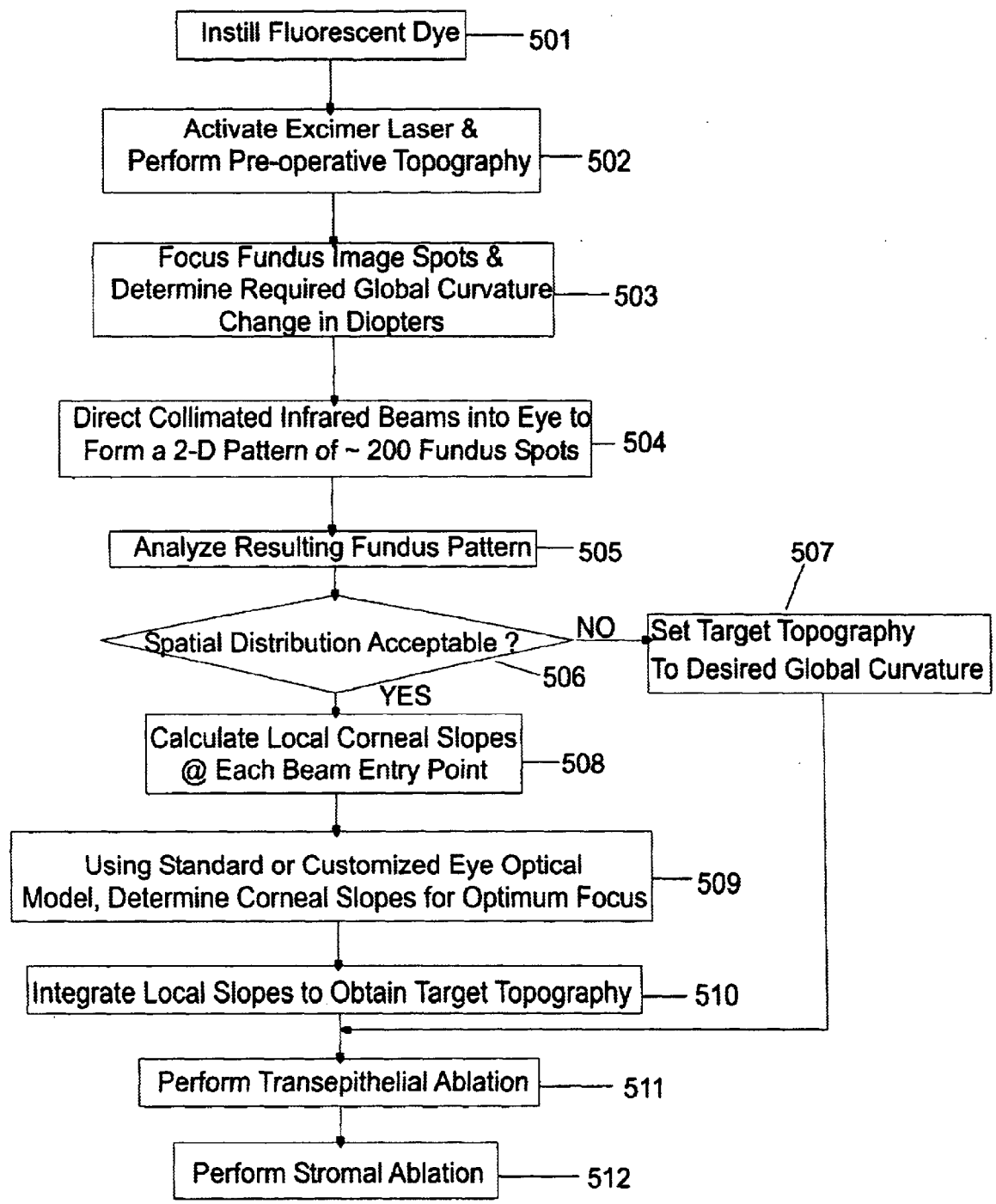
FIG. 5 is a flow diagram outlining the basic method of the invention.

FIG. 5 is a flow diagram outlining the basic steps of the method of the invention. Beginning with steps 501 and 502, a fluorescent dye is applied to the cornea of the pre-operative eye, and corneal topography performed using the same pulsed laser used for ablation and real-time topography measurement during ablation. Steps 503, 504, and 505 pertain to applying the wavefront analysis function of the invention, this function being characterized by directing a narrow beam of low-coherence light from SLD 25 through the same optical assembly used for ablation and directing each resulting collimated beam to a different position on the cornea and measuring the position on the fundus of the spot of light produced, this measurement being made only during the time interval that the eye position remains within a sufficiently small band about a selected nominal eye position. In step 503, the axial position of CCD 16 is adjustied to minimize the separation of fundus spot positions and thereby determining the corneal global curvature change in diopters required for a best achievable focus. At this axial position, a pattern of some 200 fundus spot locations is produced in step 504, in step 505 the distribution of these spot locations is analyzed, and in step 506, it is determined whether the corneal irregularities are excessive—if so, the target corneal curvature in step 507 is set to the value determined in step 503 and used as the template for the ablating process. If the magnitude of the corneal surface irregularities is acceptable, then for step 508, the localized slopes of the cornea are computed for each SLD beam entry point. Next, in step 509, a ray trace is performed using these local corneal slopes slopes together with a best approximation the remaining optical elements of the patient's eye. Then, an adjustment to the local corneal slopes is made to converge all the rays to a single spot on the fundus/retina/macula. In step 510, an integration of these desired slopes is performed to produce the desired 3-D target surface to be ablated onto the anterior stromal surface. In step 511 the epithelium is ablated down to the stromal layers after which stromal ablation in step 512 proceeds to match the target topography of the cornea. A final adjustment is made to the target topography by slightly increasing the stromal surface curvature in order to compensate for the decrease in curvature that will occur with regrowth of the epithelium.

Having defined the desired stromal surface topography, the iterative procedure to ablate to this target topography generally follows the procedure outlined in U.S. Pat. No. 5,350,374. In U.S. Pat. No. 6,024,449 an infrared detection means to avoid corneal temperature build-up resulting from ablation is disclosed. Because of the ability in the present invention to place the beam at any point on the cornea in less than a millisecond, ablation areas can be varied in a manner to minimize stromal hot-spots. An interleaved raster scan is employed for epithelial removal to avoid localized areas of corneal overheating.

Figure 6:
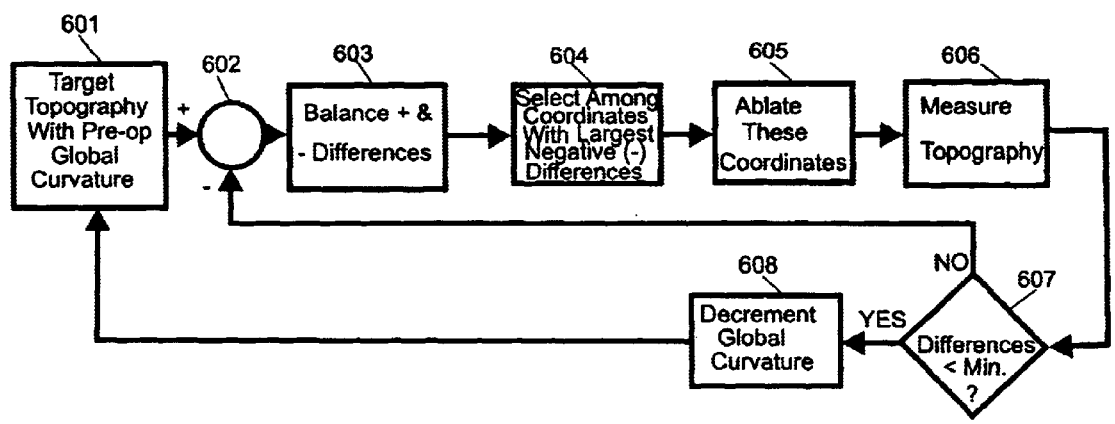
FIG. 6 is a flow/control diagram for the topography controlled scanning beam ablating procedure.

FIG. 6 is a flow/control diagram for topography controlled stromal ablation. The beginning step 601 is to take the table of coordinates representing the target corneal topography result of FIG. 5 and modify them by re-introducing the pre-operative global curvature determined from the wavefront measurement. These modified coordinates form a starting target stromal surface. Next, the coordinates obtained by the real-time topography system are differenced, step 602, with these target surface coordinates and by—in effect—axially translating the target surface into the actual (measured) stromal surface to produce about an equal number of positive and negative x and y coordinate differences as in step 603. Those that are negative represent areas to be ablated—they can be considered as islands scattered over the stromal surface. Then by directing the ablating beam to the points of largest difference, as in step 604,—in effect going successively from island to island and ablating off the peaks, as in step 605, until no negative differences exist between target and stromal surface—localized heat buildup can be minimized, and further, the attendant plumes resulting from ablation will have less interfering effect with the ablating beam. After this process has continued until negligible negative differences remain as determined by real time topography measurement (steps 606 and 607), the target surface coordinates are updated by decrementing the global curvature, step 608, introduced at the start. The procedure continues until the final target topography is imparted onto the stromal surface.

An alternate embodiment applicable to the present invention was envisaged in U.S. Pat. No. 6,024,449. Here, a topography system which, rather than imagining the diffusely reflected 193 nm raster pattern, used the 320 nm fluorescent raster image resulting from threshold stromal ablation (i.e. 193 nm around 30 mJ/cm$^2$). This approach has the advantage of avoiding all remaining speckle effects due to the 193 nm UV laser radiation; however a disadvantage arises because a higher power excimer laser would be required to increase the intensity of the raster pattern near to the threshold value.

Within the scope of the invention and/or its preferred embodiment, applications in addition to PRK can encompass laser assisted in-site keratomileusis (LASIK), laser assisted epithelial keratomileusis (LASEK) and photo therapeutic keratectomy. Also, the system and method of the invention is not restricted to in-vivo corneal tissue—customized contact lenses could be manufactured to exacting tolerances. Advancements in piezoelectric and magnetostrictive technology will likely offer drive systems in the future faster than that provided by the loudspeaker-derived means of the preferred embodiment. Advancements in laser technology would envision smaller units capable of being tuned to wavelengths and pulse rates most optimal for corneal ablation. Also advances in both digital an analog technology could be applied to either widening the bandwidth of the control and detection devices of the preferred embodiment or modifying the manner of algorithmic control without departing from the functional novelty of the invention.

I claim:

1. A system combining wavefront eye measurement and multi-loop feedback-controlled scanning photoablation under controlled real-time topography comprising:

A high pulse rate laser to produce a narrow pulsed beam having an ultraviolet wavelength capable of ablating the anterior cornea of the eye;

a continuous wave laser forming a narrow continuous beam of visible or infrared light, this continuous beam being coaxially aligned with said pulsed beam to form a combined beam;

a beam directing means comprising linear actuators to dynamically control a two-axis tiltable mirror, tilting said tiltable mirror about a pivot point in order to reflect said combined beam to a stationary parabolic mirror, said parabolic mirror having said pivot point as its focal point, from said parabolic mirror, said combined beam being reflected into collimated beams, each collimated beam able to be directed to any point of the cornea, each collimated beam position being determined by a distinct tiltable mirror position, said tiltable mirror position being measured by two tiltable mirror position detectors;

a beam splitter means to separate said collimated beams into collimated pulsed beams and collimated continuous beams, said collimated continuous beams being reflected by said beam splitter to a two dimensional controlled-photosensor, the collimated pulsed beams being transmitted through the beam splitter to the cornea, said controlled-photosensor detecting positions of impingement of the collimated continuous beams in a plane normal to said collimated continuous beams, said positions of impingement on said controlled-photosensor having a one-to-one correspondence to positions of impingement of the collimated pulsed beams on the cornea;

a raster-videokeratography means to project a pattern upon the cornea, selected pulses of said pulsed beam being diverted to a beam expander, said expander producing a slightly diverging beam, said diverging beam passing through a Ronchi bar grating to produce a diffusely reflected vertical bar pattern on the cornea, said pattern, after reflection from a dielectric or dichroic mirror, is then imaged by a field-flattening aspherical lens onto a two-dimensional ultraviolet (UV) sensor, said aspherical lens providing sharp focussing of said pattern over the entire cornea on said UV sensor, said UV sensor being comprised of rows of horizontal linear charge coupled devices (CCD's), said rows being about equal in number to the bars in said bar grating, said UV sensor so designed to maximize measurement accuracy of the pattern while minimizing measurement time;

an eye-movement detection means consisting of a scleral mask, said mask adapted to adhere to the sclera of the eye, said mask bearing reference markings, said markings being imaged by a focussing lens onto a segmented charge coupled device (SCCD);

transepithelial ablation detection means using said focussing lens to image a fluorescent 460 nm pattern produced by pulsed beam ablation of the corneal epithelium, said 460 nm pattern being imaged on a regular charge coupled device (CCD), said regular CCD having a uniform two-dimensional pixel distribution;

a wavefront measurement means using a low spatial coherence light source in place of the pulsed laser beam, said low spatial coherence light source being collimated into narrow low coherence beams, said light source using said beam directing means to form a plurality of light spot images on the fundus of the eye, said spot images being focussed through said focussing lens onto the regular CCD;

a feedback control means for controlling both said collimated pulsed beams and said low coherence beams comprising both passive and active analog devices and digital processor devices.

2. The system of claim 1 where the tiltable mirror is bottom supported at a fixed pivot, this fixed pivot point being close enough to a reflecting surface point on the tiltable mirror so that this surface point remains substantially fixed in space regardless of mirror tilt angle, where said combined beam is directed at said surface point, where the bottom of the mirror is firmly connected at one end of a coil spring under tension, where other end of the spring is firmly attached to a reference base, where at periphery of said tiltable mirror and separated by 90° are two movable pivots, position of said pivots being controlled by said linear actuators, the position of said pivots and thereby said tiltable mirror being sensed by said mirror position detectors.

3. The system of claim 1 where each of said linear actuators comprises a cylindrical coil of electrically conductive wire, said coil being centered within an airgap, said airgap having a uniform magnetic field, said field being provided by a neodymium-iron-boron permanent magnet structure.

4. The system of claim 1 where said pulsed laser is an excimer laser operating at 193 nm wavelength with pulse rates upwards of 500 pulses per second and pulse energy in region of 10 mJ, where said continuous wave laser is a diode pumped solid state 532 nm type operating at about 5 mW.

5. The system according to claim 1 where the beam splitting means is a wideband polarizing beam splitter, where said pulsed beam and said continuous beam are both plane-polarized with axes of polarization rotated 90° with respect to each other.

6. The system according to claim 1 where said scleral mask is provided with uniformly distributed projections adapted to pierce the epithelium, where said reference markings are comprised of a substance fluorescing at 570 nm, said substance being applied to thin rigid titanium bars the same size as said markings, said bars mounted on thin semi-flexible walls, said walls attached to said mask in a manner to maintain scleral adhesion.

7. The system according to claim 1 where said SCCD comprises six linear CCD segments, four of the segments arranged to detect translational movement in the reference markings of the scleral mask and two of the segments arranged to detect rotational movement in the reference markings of the scleral mask.

8. The system according to claim 1 where the raster-videokeratography UV sensor means is a back-illuminated charge coupled device (BCCD) sensitive in the 193 nm range, said sensor consisting of some 50 horizontal rows of pixels delimited within a circular boundary, each row being one pixel wide, at a horizontal spacing of approximately 500 pixels per mm relative to the corneal surface.

9. The system of claim 1 where said low spatial coherence light source is a super luminescent diode producing low spatially coherent light at a wavelength of 780 nm.

10. The system according to claim 1 where said transepithelial ablation detection means and said wavefront measurement means are switchable from the one means to the other by switching from a 570 nm dichroic mirror transmitting the reference marking light and reflecting the 460 nm epithelial ablation fluorescence, to a second dichroic mirror similarly transparent to 570 nm while being reflective to said low coherence beam.

11. The system of claim 1 where said controlled-photosensor is a two-dimensional charge injection device (CID), said CID transmitting intensities of only pixels preselected by signals from the tiltable mirror position detectors.

12. The system of claim 1 where the mirror position detectors are electret sensors.

13. The system of claim 1 where said focussing lens is transmissive to light over a range of wavelength from about 193 nm to 1000 nm to accommodate all imaging requirements of the system.

14. The system of claim 1 where the wavefront measurement means further comprises a controlled linear positioner, in order to move said regular CCD to achieve minimum separation among the fundus spot images; where the wavefront measurement means further comprises an eye fixation target, said fixation target located behind said SCCD, said SCCD having a central hole, said hole enabling a patient to fixate on the fixation target in order to reduce eye movement.

15. The system of claim 1 where said digital processor devices include three programmable logic devices (PLD): The first PLD, PLD1 performs about 30000 eye position computations per second using pixel intensity signals from the SCCD, a second PLD, PLD2 computes the beam position on the cornea from pixel intensity signals from the controlled-photosensor about every 40 μsec, a third PLD, PLD3 computes the real-time corneal topography from pixel intensity signals from the BCCD about 5 times per second.

16. A method for conducting scanning photoablation of a corneal surface under real-time feedback topographic control to produce a cornea surface as determined by wavefront analysis comprising the steps:

Placing on a pre-operative eye a scleral mask having reference markings and activating an eye tracking means insuring that exact position of the eye is known at all instants throughout all measurement and operative procedures;

conducting wavefront analysis by directing narrow collimated low coherence light beams through a pre-operative cornea onto the fundus of the eye producing a light spot pattern, recording the light spot position on the fundus of the eye for each beam;

measuring the topography of the cornea by applying a fluorescent dye to the pre-operative cornea and, by using a raster-videokeratography means, determining the topography of the pre-operative cornea;

determining a best-focus global curvature change for the pre-op cornea;

performing ray trace calculations on an optical model best representing the pre-operative cornea producing a calculated fundal spot pattern, next comparing this calculated spot pattern with the spot pattern obtained by the wavefront measurement, then calculating a modified pre-op corneal topography to minimize spot pattern spread, said modified topography yielding a final desired corneal template;

performing scanning transepithelial ablation by monitoring the presence of 460 nm fluorescence produced by 193 nm radiation, continuing ablation only on those areas still emitting the 460 nm fluorescence until the 460 nm component drops below a threshold for all areas;

conducting stromal ablation of the cornea by: setting the global curvature determined for the pre-operative cornea as a starting template, measuring the topography of the cornea comprising a set of some 2000 elevation values by employing the same raster-videokeratography means used for pre-operative topography measurement, differencing these elevation values with those of the template, forming a table, using said table to identify the corneal sectors to be ablated and the depth of ablation required to minimize said differences, then controlling the scanning ablation pattern among said sectors to maximize spatial separation between consecutive ablating pulses;

modifying the global curvature of said starting template to produce an intermediate template between said initial template and the final desired template and reiterating said stromal ablation procedure, and continuing to modify further portions of the global curvature until said intermediate template matches said final desired template and the ablated cornea matches the desired topography.

17. The method of claim 16 where the step of determining a best-focus global curvature includes the steps of: Moving a CCD used in wavefront analysis to an axial position from a focussing lens to minimize the spot pattern area, and correlating said axial position with said pre-operative topography to yield a global curvature of the cornea needed for best obtainable vision exclusive of wavefront correction.

18. The method of claim 16 where the steps of wavefront analysis, epithelial or stromal ablation are conducted under the following feedback control steps: Focussing said reference markings on a CCD, sensing resulting CCD intensity analog signals, converting these analog signals to digital form, using a digital processing means, calculating, translational and axial rotational coordinates of eye position every 30 usec for less, converting these digitally calculated coordinates into analog form giving two time varying x and y co-ordinate signals of eye movement, inputting each time varying signal into an analog lead/lag circuit, outputting each signal from the lead/lag circuit to the input of a power amplifier, each power amplifier driving an actuator, each actuator controlling one axis of a tiltable mirror, sensing tiltable mirror position to form an analog sensing signal for each axis of said tiltable mirror, feeding back negatively through a derivative circuit to the input of each power amplifier;

directing a narrow coaxial beam of pulsed ablative radiation and continuous radiation to a pivoted point of said tiltable mirror, reflecting said coaxial beam along a path defined by a distinct tilt position of the tiltable mirror to a parabolic mirror, reflecting from said parabolic mirror the coaxial beam along paths collimated with respect to one another, separating a given collimated beam to transmit the pulsed ablative component to the cornea and reflecting said continuous component to a controlled CCD, using said analog sensing signals from said tiltable mirror to indicate a probable limited pixel area of beam impingement, constraining the controlled CCD to output the pixels within this limited area of pixel intensities, then, after converting to digital form, digitally computing beam position co-ordinates, converting the co-ordinates to analog form, inputting the co-ordinates into lead/lag compensation circuits forming compensated signals, then negatively inputting the compensated signals into the respective power amplifiers thereby completing an outer negative feedback loop to obtain precise beam positioning, inputting into derivative circuits said analog sensing signals from said mirror, negatively inputting outputs from said derivative circuits into the respective power amplifiers thereby completing an inner negative feedback loop to obtain stable, high-speed beam positioning.

19. The method of claim 16 where the step of conducting wavefront analysis also includes the step of limiting measurement of each light spot comprising said light spot pattern only to those periods of time when the eye position does not deviate more than a specified maximum incremental position about a nominal eye position.

20. The method of claim 16 where the step of measuring the topography of the cornea can include the step of limiting each topography measurement to an instant in time when the eye position resides within a specified incremental position about a nominal eye position.

* * * * *